US00PP25028P3

(12) United States Plant Patent
Blom

(10) Patent No.: US PP25,028 P3
(45) Date of Patent: Nov. 4, 2014

(54) ***CHRYSANTHEMUM* PLANT NAMED 'ZANMUFLAMINNEON'**

(50) Latin Name: ***Chrysanthemum×morifolium* Ramat.**
Varietal Denomination: Zanmuflaminneon

(71) Applicant: Chrysanthemum Breeders Association Research B.V., Aalsmeer (NL)

(72) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 13/694,698

(22) Filed: Dec. 26, 2012

(65) Prior Publication Data

US 2014/0182027 P1 Jun. 26, 2014

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Anne Grunberg
(74) *Attorney, Agent, or Firm* — Steptoe & Johnson LLP

(57) ABSTRACT

A *chrysanthemum* plant named 'Zanmuflaminneon' characterized by its medium sized blooms with bright purple ray florets and prolific branching; natural season flowering August 29 (week 35); blooming for a period of 5 weeks.

3 Drawing Sheets

Botanical designation: *Chrysanthemum×morifolium* Ramat.

Cultivar denomination: 'Zanmuflaminneon'.

RELATED CULTIVARS

The new plant is related to 'Zanmuflamin' (U.S. Plant Pat. No. 20,589). 'Zanmuflamineon' is a mutant of 'Zanmuflamin'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuflaminneon'. 'Zanmuflaminneon' is a product of a breeding and selection program which had the objective of finding color mutants from existing parent plants. The new plant comprises a natural mutant of the parent *chrysanthemum* named 'Zanmuflamin'. Plants from the new cultivar 'Zanmuflaminneon' differ from plants of the female parent in the color of the ray-florets. The color is bright purple in the mutant, while it is more subdued in the parent.

The new cultivar was discovered as a color mutant in September 2006 by Wilhelmus Bernardus Blom in a controlled environment (greenhouse) in Rijsenhout, The Netherlands. The first act of asexual reproduction of 'Zanmuflaminneon' was accomplished when after planting of the mutant as a motherplant in Rijsenhout; vegetative cuttings from this mutant were taken and propagated further. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
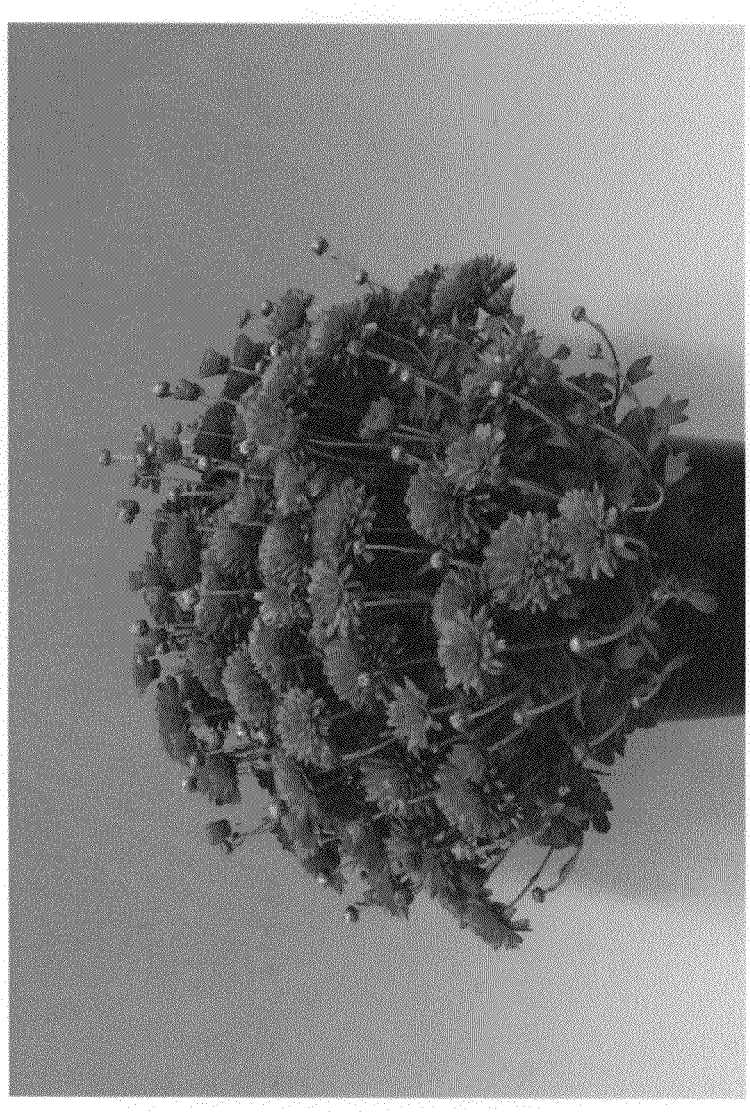
FIG. 1 shows a plant of the cultivar in full bloom.
Figure 2:
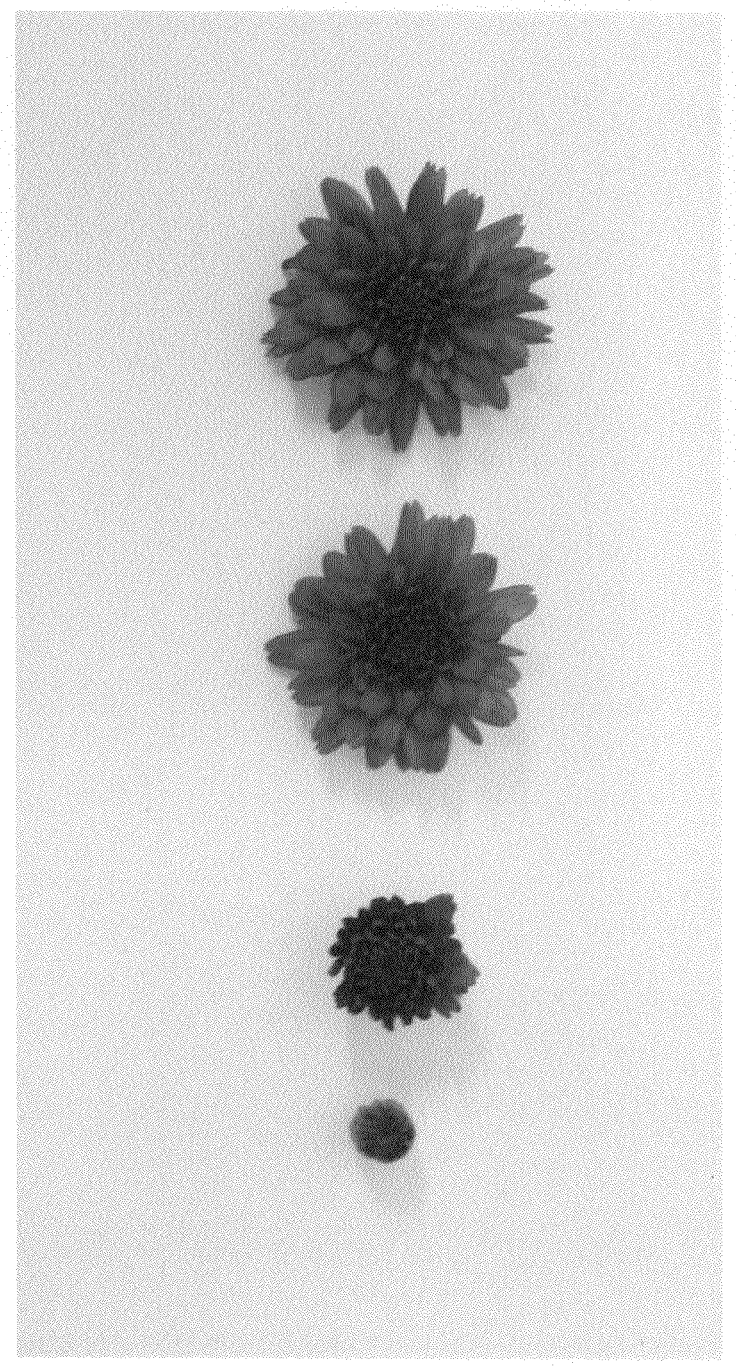
FIG. 2 shows the various stages of blooms of the new cultivar.
Figure 3:
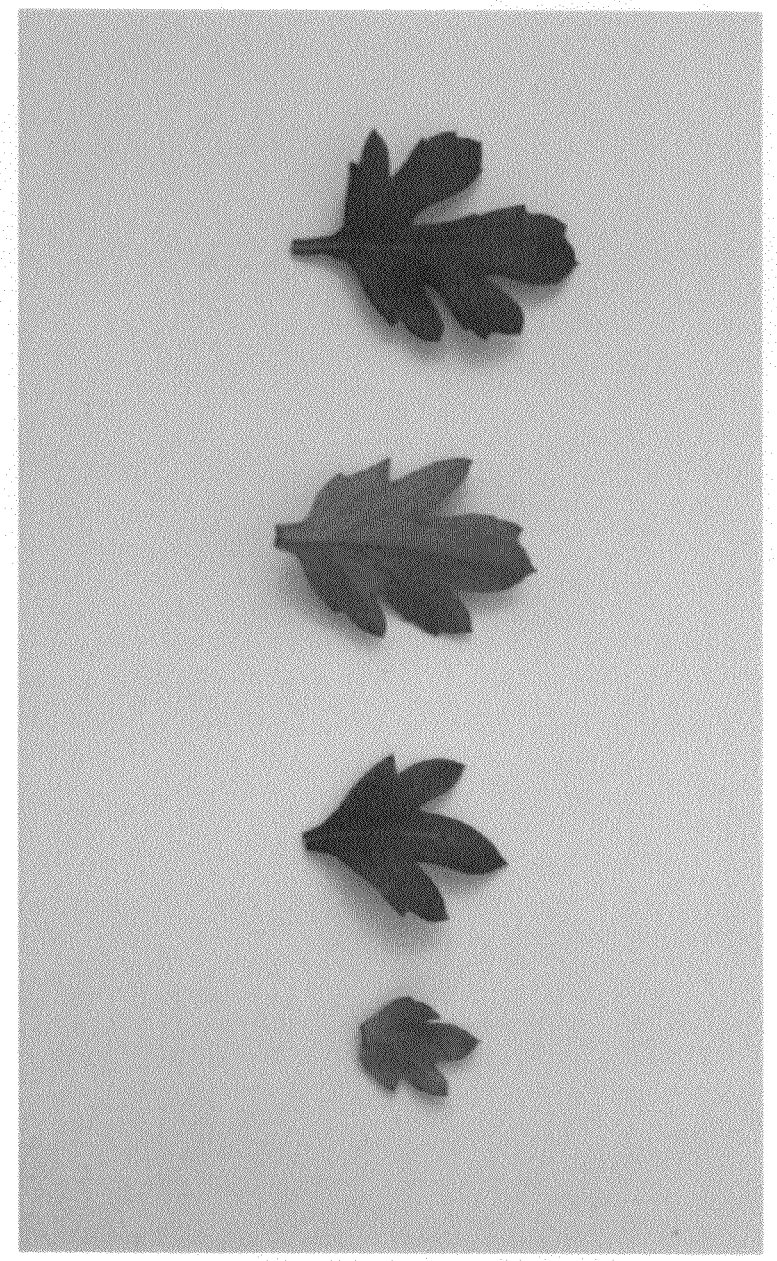
FIG. 3 shows the various stages of foliage of the new cultivar.

The observations and measurements were gathered from plants grown out door in Rijsenhout, The Netherlands, under natural day length and temperature and planted in week 22 in 2011. The natural blooming date of this crop was August 29 (week 35). The average height of the plants was 29 cm. No growth retardants were used. No tests were done on disease or insects resistance or susceptibility. No tests were done on cold or drought resistance. This new variety produces medium sized blooms with bright purple ray florets blooming for a period of five weeks.

From the cultivars known to inventor the most similar existing cultivar in comparison to 'Zanmuflaminneon' are 'Zanmuflamin' (U.S. Plant Pat. No. 20,589) and 'Zanmuflamincran' (U.S. Plant Pat. No. 23,367). When 'Zanmuflamin', 'Zanmuflamincran' and 'Zanmuflaminneon' are being compared the following difference is noticed: The ray-florets of 'Zanmuflaminneon' are more bright purple than of those of "Zanmuflamin' and 'Zanmuflamincran'.

The following is a description of the plant and characteristics that distinguish 'Zanmuflaminneon' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

TABLE 1

Botanical Description of *Chrysanthemum* x *morifolium* Ramat. 'Zanmuflaminneon'

| | |
|---|---|
| **Bud** | |
| Size: | Small; cross-section 8 mm, height 4 mm |
| Shape: | Round |
| Texture: | Pubescent |
| Outside color: | Greyed-green 191A |
| **Phyllaries** | |
| Number: | 18, arranged in 3 rows |
| Shape: | Elliptic |
| Apex: | Acute |
| Base: | Truncate |
| Margin: | Entire |
| Color: | Upper side: Greyed-green 191B<br>Lower side: Greyed-green 191C |
| Length and width: | 5 mm; 2 mm |
| Texture: | Pubescent |
| **Inflorescences** | |
| Type: | Double |
| Height: | 1.5-2.5 cm |
| Diameter: | 5 cm |
| Peduncle length: | 10-13 cm |
| Peduncle color: | Green 138B |
| Peduncle diameter: | 2 mm |
| Peduncle texture: | Pubescent |
| Number per branch: | About 5 inflorescences |
| Duration of flowering: | 5 weeks |
| Seeds: | Produced in small quantities, ovate, Greyed-brown 199A, length 1.5 mm, diameter 0.5 mm |
| Fragrance: | Faint chrysanthemum odor |
| **Color inflorescences** | |
| Center of inflorescence: | Immature stage: Red-purple 58D; Mature stage: Red-purple 64C |
| Color of upper side of ray florets: | Red-purple 64D |
| Color of lower side of ray florets: | Greyed-purple 186D at base to Greyed-purple 186B at apex |
| Tonality from distance: | A garden mum with bright purple blooms |
| Color of ray florets after aging of the plant: | Greyed-purple 186C |
| **Ray florets** | |
| Texture: | Upper and lower side smooth |
| Number: | 190-200 |
| Shape: | Elliptic |
| Apex: | Dentate |
| Base: | Attenuate |
| Cross-section: | Flat |
| Longitudinal axis: | Straight |
| Length of corolla tube: | 4 mm |
| Ray floret margin: | Entire |
| Ray floret length: | 1.5-2 cm |
| Ray floret width: | 4-5 mm |
| Ratio length/width: | High |
| Disc florets | Absent |
| **Receptacle** | |
| Color: | Yellow-green 145D |
| Shape: | Domed raised |
| Height: | 3 mm |
| Diameter: | 3 mm |
| **Reproductive Organs** | |
| Androecium: | Absent |
| Gynoecium: | Present in ray florets |

TABLE 1-continued

Botanical Description of *Chrysanthemum* x *morifolium* Ramat. 'Zanmuflaminneon'

| | |
|---|---|
| Style color: | Yellow-green 154C |
| Style length: | 3 mm |
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Medium |
| Height: | 28-30 cm |
| Width: | 38-40 cm |
| Stem color: | Greyed-brown 199A |
| Stem strength: | Strong |
| Stem brittleness: | Not brittle |
| Stem anthocyanin coloration: | Only in mature plants |
| Internode length: | 2-2.5 cm |
| Length of lateral branch: | From top to bottom 18 cm |
| Lateral branch color: | Green 137 C |
| Lateral branch, attachment: | Brittle |
| Lateral branch diameter: | 3 mm |
| Branching (average number of lateral branches): | Prolific with 8 breaks after pinching |
| Natural season blooming date: | August 29 (week 35-39) |
| **Foliage** | |
| Leaf color: | Upper side: Green 138A; Lower side: Green 139C |
| Color midvein: | Upper side: Yellow-green 147D; Lower side: Yellow-green 148D |
| Size: | Small; length 3.5-4 cm, width 2-2.5 cm |
| Quantity (number per lateral branches): | 16-18 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Truncate |
| Apex: | Mucronulate |
| Petiole length: | 0.5-1 cm |
| Petiole diameter: | 2 mm |
| Petiole color: | Yellow-green 147D |

TABLE 1

Difference with comparison varieties (when grown under identical conditions)

| | 'Zanmuflaminneon' | 'Zanmuflamincran' | 'Zanmu-flamin' |
|---|---|---|---|
| Color upper side ray-florets | Red-purple 64D | Red 47A, with Yellow 6B at base | Red-purple 59D |

I claim:

1. A new and distinct variety of *chrysanthemum* plant as described and illustrated.

* * * * *